United States Patent
Reichmann et al.

(10) Patent No.: US 10,953,140 B2
(45) Date of Patent: Mar. 23, 2021

(54) TISSUE GRAFT

(71) Applicant: UNIVERSITAT ZURICH, Zurich (CH)

(72) Inventors: Ernst Reichmann, Adligenswil (CH); Daniela Marino, Zurich (CH); Agnieszka Sylwia Klar, Dietlikon (CH)

(73) Assignee: UNIVERSITAT ZURICH, Zurich (CH)

( * ) Notice: Subject to any disclaimer, the term of this patent is extended or adjusted under 35 U.S.C. 154(b) by 593 days.

(21) Appl. No.: 15/500,106

(22) PCT Filed: Jul. 29, 2014

(86) PCT No.: PCT/EP2014/066258
§ 371 (c)(1),
(2) Date: Jan. 30, 2017

(87) PCT Pub. No.: WO2016/015754
PCT Pub. Date: Feb. 4, 2016

(65) Prior Publication Data
US 2017/0258965 A1   Sep. 14, 2017

(51) Int. Cl.
| | | |
|---|---|---|
| *A61L 27/60* | (2006.01) | |
| *A61L 27/22* | (2006.01) | |
| *A61L 27/24* | (2006.01) | |
| *A61L 27/38* | (2006.01) | |
| *A61L 27/52* | (2006.01) | |
| *A61L 27/50* | (2006.01) | |
| *A61L 27/36* | (2006.01) | |
| *G01N 33/50* | (2006.01) | |

(52) U.S. Cl.
CPC .............. *A61L 27/60* (2013.01); *A61L 27/225* (2013.01); *A61L 27/24* (2013.01); *A61L 27/3691* (2013.01); *A61L 27/3804* (2013.01); *A61L 27/3808* (2013.01); *A61L 27/3813* (2013.01); *A61L 27/3834* (2013.01); *A61L 27/3891* (2013.01); *A61L 27/50* (2013.01); *A61L 27/52* (2013.01); *G01N 33/5005* (2013.01)

(58) Field of Classification Search
CPC ........ A61L 27/60; A61L 27/225; A61L 27/24; A61L 27/3691; A61L 27/3804; A61L 27/3808; A61L 27/3813; A61L 27/3834; A61L 27/3891; A61L 27/50; A61L 27/52; G01N 33/5005
USPC ....................................................... 435/325
See application file for complete search history.

(56) References Cited

FOREIGN PATENT DOCUMENTS

| WO | WO/2000/062833 | 10/2000 |
|---|---|---|
| WO | WO/2011/154687 | 12/2011 |

OTHER PUBLICATIONS

Schiestl et al., Formation of human capillaries in vitro: The engineering of prevascularized matrices, Tissue Engineering, Part A, vol. 16, No. 1, (2010), pp. 269-282.*
Böttcher-Haberzeth et al., Tissue engineering of skin, Burns 36, 450-460 (2010).
Braziulis et al. 2012 (Modified Plastic Compression of Collagen Hydrogels Provides an Ideal Matrix for Clinically Applicable Skin Substitutes, Tissue Engineering: Part C; vol. 20 18, No. 6, 2012).
Braziulis et al. 2011 Skingineering I: engineering porcine dermo-epidermal skin analogues for autologous transplantation in a 25 large animal model, Pediatr. Surg. Int. (2011) 27:241-257).
Klar et al. 2014, Tissue-engineered dermo-epidermal skin grafts prevascularized with adipose-derived cells, Biomaterials. Jun. 25, 2014;35(19):5065-78).
Marino et al. 2014, Bioengineering dermo-epidermal skin grafts with blood and lymphatic capillaries, Sci Transl Med. Jan. 29, 2014;6(221):221ra14.
Pontiggia L et al. Journal of Investigative Dermatology (2009) 129, 480-490; doi:10.1038/jid.2008.254; published online Aug. 21, 2008).
Schiestl et al., 2011 (Skingeineering II: transplantation of large-scale laboratory-grown skin analogues in a new pig model, Pediatr. Surg. Int. (2011) 27:249-254)).
Engelhardt et al., Biomaterials 32(16) 2011, p. 3969-3976: A collagen-poly(lactic-co-e-caprolactone) hybrid scaffold for bladder tissue regeneration.
Marino et al., J Tissue Eng Regen Med 2014, 8 (Suppl. 1). p. 97-98, abstract No. OP107: Bioengineering dermo-epidermal skin grafts with blood and lymphatic capillaries.
Zhao Liang et al. Research progress of wound biological dressing and artificial skin; Fujian Normal University Journal (national science edition), No. 1, vol. 27.
Wei Gangqiang et al. Research and clinical application of artificial skin used outside burn wound; Chinese Tissue Engineering Research and Clinical Rehabilitation No. 19, vol. 12.
Zhao Guangjian et al. Material type and characteristics of artificial skin substitutes; Chinese Tissue Engineering Research and Clinical Rehabilitation No. 29, vol. 14.

* cited by examiner

*Primary Examiner* — Jennifer M. H. Tichy
(74) *Attorney, Agent, or Firm* — JMB Davis Ben-David

(57) ABSTRACT

The present invention is directed to a method of producing a tissue graft, comprising at least steps of providing a gel, seeding the gel with cells of at least a first and/or cells of a second type, and culturing of the cells of the first and/or cells of the second type in said gel until the formation of at least one first biostructure in the gel by the cells of the first type and/or the cells of the second type.

20 Claims, 8 Drawing Sheets

Assembly of flask

Assembly of compresion device

Compression

Gel Transfer

TISSUE GRAFT

CROSS-REFERENCE TO RELATED APPLICATIONS

This is the U.S. National Stage of International Application No. PCT/EP2014/066258, filed Jul. 29, 2014, which was published in English under PCT Article 21(2).

TECHNICAL FIELD

The present invention relates to a device containing at least one biostructure, and a method of making the device, for use in therapeutic treatment and/or for in vitro testing of human or other mammalian tissues. For example, the device may be used on skin wounds for burned, injured, or diseased skin, and provides structures and functions as in normal uninjured skin

PRIOR ART

Human skin is composed of three main layers: the epidermis (outermost), the dermis (middle) and the hypodermis (deeper most). When a deep wound is created (full-thickness skin wound), after e.g. a burn accident, the epidermis and the full dermis (in some cases also the hypodermis) are damaged and surgical intervention is required. Small full-thickness skin wounds are optimally treated by means of full-thickness skin autografts: epidermis and whole dermis are harvested from a healthy part of the body and transplanted on the wound. In contrast, large full-thickness skin defects, treated by means of split-thickness skin autografts (which consist of epidermis and only a very and incomplete thin layer of dermis), still represent a clinical unsolved issue. Indeed, such wounds heal badly and develop into large, disfiguring and unfunctional scars. Many are the reasons why the full-thickness skin autografts optimally heal deep wounds in contrast to split-thickness autografts. One of these reasons is to be found in the presence of vascular structures in the full- and the lack of those in the split-thickness autografts. Vascular biostructures (blood and lymphatic vessels) are essential for the organs in the human body, by constantly providing oxygen and nutrients as well as immune cell trafficking, they contribute to full functionality and survival. The same is valid for transplanted organs, even for thin and flat organs such as skin. The capillaries in the full-thickness skin grafts only need to connect to the capillaries of the wound bed, while in the case of split-thickness skin grafts, the capillaries need to ingrow the graft in order to perfuse the tissue.

Recently, research and clinical evidence has also suggested that the lymphatics may be necessary for skin graft survival, by essentially draining immune cells, debris, and excess fluid from the wounded area. When thinking of a way of providing large quantities of full-thickness skin grafts for the treatment of large full-thickness skin defects, tissue engineering of skin containing vascular biostructures comes into play. One of the main advantages of a hydrogel as a scaffold material (versus other kinds of scaffold, e.g. collagen sponges) is its properties as a 3D cell substrate. It is highly biocompatible and biomimetic, has low immunogenicity (conserved across species) and is naturally remodelled by cells which can be easily seeded interstitially within the fibril network. However, the poor mechanical properties of hydrogels are a major limitation in their clinical use as scaffolds for tissue engineering applications.

Mechanical stability is essential for the clinical application of tissue engineered products based on hydrogels, especially when these products are characterized by large and thin physical dimensions as in the case of skin grafts (a clinical relevant size for a skin graft is min. 50 cm$^2$ with a thickness of less than 2 mm).

Mechanical stability is required to allow handling and processing of a hydrogel during and after culturing as well as during and after surgical application and/or testing. Mechanical stability of gels can be increased by compaction. EP 0 187 104 discloses the compression of a collagen gel matrix to form a fiber network for medical use. EP 1 773 416 discloses the use of plastic compaction of a gel in the preparation of scaffold-cell matrices for tissue implants.

Braziulis et al. 2012 (Modified Plastic Compression of Collagen Hydrogels Provides an Ideal Matrix for Clinically Applicable Skin Substitutes, Tissue Engineering: Part C; Vol. 18, No. 6, 2012) reported on a modified plastic compression method for the engineering of hydrogel-based large, 7×7 cm, human dermo-epidermal skin grafts. These compressed engineered products showed optimal mechanical stability during and after cell culture phase, as well as during transplantation phases on pigs (Braziulis et al. 2011 Skingineering I: engineering porcine dermo-epidermal skin analogues for autologous transplantation in a large animal model, Pediatr. Surg. Int. (2011) 27:241-257), Schiestl et al., 2011 (Skingeineering II: transplantation of large-scale laboratory-grown skin analogues in a new pig model, Pediatr. Surg. Int. (2011) 27:249-254)). Astonishingly, the biological properties of the cells seeded in and on the hydrogels were not altered by the compression process.

SUMMARY OF THE INVENTION

It is an aim of the invention in general to produce an improved and mechanically stable tissue graft device containing cells and at least one biostructure in and/or on a preferably biocompatible, biodegradable hydrogel matrix for clinical use in humans and/or testing. More specifically, it is an aim to develop a, preferably autologous, dermo-epidermal skin graft with biostructures for clinical use and testing.

So far, prevascularized dermo-epidermal skin substitutes containing blood vascular biostructures have been generated for research purposes. No data is available on the bioengineering of prevacularized dermo-epidermal skin grafts for intended clinical use for the treatment of skin defects.

Additionally so far, limited data is available on the engineering of human lymphatic capillaries and no data is available on the bioengineering of prevascularized dermo-epidermal skin substitutes containing functional human lymphatic capillaries. In the human dermis, lymphatic vessels play a major role in tissue fluid homeostasis and immune cell trafficking. Dermal lymphatic capillaries exhibit a wide lumen, anchoring filaments, and no or an incomplete basement membrane, and lack mural cell coverage. These features enable lymphatic capillaries to respond to interstitial liquid pressure by taking up and removing excess tissue fluid. After wounding, also the lymphatic endothelium is ruptured; thus, the draining capacity of the lymphatic vessels is compromised. As a consequence, accumulation of tissue fluid arises. Persistent local interstitial fluid, as well as delayed removal of local debris and inflammatory cells, impedes wound healing. In contrast, induction of lymphangiogenesis and immune cell recruitment were shown to accelerate skin regeneration.

A first embodiment of the invention is directed to a method of producing a tissue graft, comprising at least the following steps:
   providing a gel,
   seeding the gel with cells of at least a first type and/or cells of a second type,
   culturing the cells of the first type and/or cells of the second type in said gel until the formation of at least one first bio structure in said gel by the cells of the first type and/or the cells of the second type.

In other words, the gel is seeded with one or more cell types and the cells are cultured in and/or on said gel until the formation of at least one type of biostructure. The gel used for the method of the invention can be any 3D biomatrix, such as a collagen hydrogel, preferably of type I collagen, or a fibrin hydrogel.

In biology, structures exist at all levels of organization, ranging hierarchically from the atomic and molecular to the cellular, tissue, organ, organismic, population and ecosystem level. For the purpose of this application, the term "biostructure" is to be understood as any structure/tissue/organ, which is composed of more than one cell, present in the human or other mammalian body/embryo/fetus, having some kind of organization and/or complexity and/or functionality. A mere random cluster of cells therefore would not fall under this definition.

The results presented in this application show data for the formation of human vascular and epidermal biostructures in and/or on the gel, respectively.

However, the system according to the present invention can be used to engineer biostructures of any type present in the human or other mammalian body/embryo/fetus, e.g. epithelial (including glandular, placental and amniotic), vascular (blood and lymphatic vessels), nervous, connective tissue (including bone), hair, nail and tooth, mesenchymal, muscular, adipose, and all human or other mammalian organs and tissues.

The formation of the (one or more types of) biostructures can be induced by the seeding and culturing of all kinds/types of human or other mammalian cells and their mixture, which can include: cells of endodermal origin, cells of mesodermal origin, cells of ectodermal origin, including the neural crest, cells of trophoblast origin, germ cells, stem cells, progenitor cells, genetically modified cells, etc., wherein the cells to be seeded have a biostructure-forming capacity.

The selection of cells or the combination of cell types used for seeding the gel is dependent on the type of tissue to be engineered.

In a preferred embodiment, the first biostructure is formed in the gel. It is also possible that more than one type of biostructure is/are formed (in or on the gel).

In a further preferred embodiment, the first biostructure/first type of biostructure is a vascular structure, preferably a vascular plexus of blood and/or lymphatic capillaries, preferably of both.

Cells of the first type and/or of the second type (and/or more types), which are to be seeded into the hydrogel, for the induction of at least the first biostructure (or more than one type of biostructure), can be any of the cell types present in a body/embryo/fetus, preferably in the human or other mammalian body. Preferably, the cells of the first type and/or of the second type (and or more types) are selected from the group of endothelial cells, epithelial cells, fibroblasts, mesenchymal cells, hematopoietic cells, cells of the immune system, adipose tissue-derived cells, mural cells, stem cells, progenitor cells, genetically modified cells. It is also possible that cells of more types (than two) are used, and mixtures of various types, i.e. more than two types, might be necessary for the induction/creation of the at least one, possibly more than one biostructure (of one or more types) in and/or on the gel.

For the induction of a vascular biostructure, preferably a mix of endothelial cells and fibroblasts is used. In other words, according to an especially preferred embodiment, the cells of the first type are endothelial cells and the cells of the second type are fibroblasts. The endothelial cells and the fibroblasts are then co-cultured together in the gel for formation of the first biostructure. Preferably, the endothelial cells and the fibroblasts are seeded and co-cultured in the gel with a ratio of fibroblasts to endothelial cells of at least 3:7, preferably of at least 2:3, more preferably about 1:1.

The endothelial cells preferably are human blood vascular endothelial cells (hBEC's) and/or human lymphatic endothelial cells (hLECs), preferably human dermal microvascular endothelial cells (HDMECs) or SVF derived. HDMECs consist of a mixture of both hLEC's and hBEC's, so both types of functional capillaries—blood and lymph—formed from these cells in vitro in the fibrin or collagen hydrogels. Another possible source of cells is the SVF, which are a mixture of blood endothelial cells, fibroblasts and mural cells in a patient's specific ratio, leading to the formation of functional blood capillaries in vitro in the fibrin or collagen hydrogels.

The formation of all kinds of biostructures can be induced in the hydrogel system according to the present invention. The formation of biostructures can be induced by seeding and culturing of cells on and/or in the hydrogel.

All or part of the cells and biostructures may be autologous, meaning that their origin is the recipient of the cultured device (the patient to be treated with the graft). Autologous cells are isolated from the same human or other mammalian body as the body to be treated with the replacement tissue graft. Autologous transplantation advantageously eliminates concerns about the tissue compatibility and rejection.

According to a further preferred embodiment, cells of a third type (or more types) are seeded onto the gel after the at least one first biostructure has been formed (at least partially or completely) in the gel by the cells of the first type and/or the cells of the second type. After seeding of the cells of the third type the gel preferably is cultured in a suitable medium until the formation of at least one second biostructure in and/or on the gel, preferably on the gel. However, transplantation also is possible before the second biostructure is partially or completely formed. The second biostructure can be of the same type than the first biostructure, however, it preferably is a biostructure of a different type (than the type(s) of biostructure formed by the cells of the first and/or second cell type). Preferably the second biostructure, formed by/of the cells of the third type, is an epidermal structure.

Preferably, the gel is co-cultured with the respective cells in a flask containing a suitable cell culture medium for the cell growth of the specific cell type(s).

Cells of the third type, which are to be seeded onto the hydrogel, for the induction of at least a second biostructure, generally can be of any of the cell types present in a body, preferably in the human or other mammalian body. The cells of the third type (or more types) can be of the same and/or different type(s) than the cells seeded for the formation of the first biostructure. Preferably, for the induction of an epidermal biostructure, keratinocytes are used. However, other possible cells are e.g. melanocytes, merkel cells, cells of the immune system, adipose tissue-derived cells, epithelial cells not derived from epidermis, stem cells, progenitor cells, genetically modified cells, etc.

Preferably the cells of a first type and/or of a second type and/or of a third (or further) type are mammalian cells, most preferably human cells. It is especially advantageous if the cells used to seed the gel are autologous cells.

The above mentioned method according to a specifically preferred embodiment, is directed to the in vitro bioengineering and in vivo grafting of a human dermo-epidermal skin substitute prevascularized by blood and/or lymphatic capillaries, preferably both. Both a pure population of hLECs (isolated from human foreskin) and a hLEC fraction present in HDMECs(isolated from human foreskin) developed into lumen forming bona fide lymphatic capillaries in vitro within 21 days in either fibrin or collagen type I hydrogels. The lymphatic nature of the engineered microvessels was confirmed by showing that they presented anchoring filaments, expressed all major lymphatic markers, and could be modulated by both lymphangiogenic and anti-lymphangiogenic stimuli. Lymphatic functionality was confirmed by demonstrating that the bioengineered lymphatic microvessels took up fluid from the interstitial space in vitro and triggered fluid drainage in vivo. Grafting studies in vivo revealed that the engineered lymphatic microvessels maintained their lumens as well as their typical characteristics, such as the absence of a complete basement membrane and the lack of mural cell coverage. Bioengineered human lymphatics were found to anastomose to the recipient's lymphatics as early as 14 days after transplantation. When transplanted onto immunoincompetent rats, the prevascularized dermis supported the development of the epidermis, indicating that it may, in the future, be possible to translate these prevascularized dermo-epidermal substitutes into clinical application.

Additionally, blood capillaries can be engineered in the hydrogel by using the stromal fraction of vascular human adipose tissue (SVF). SVF cells have shown a high vasculogenic potential. SVF cells developed into a functional capillary plexus in human dermo-epidermal skin grafts. After transplantation, graft take and remodeling upon rapid graft perfusion supported survival and functionality of the transplanted graft.

So far, no data is available on the bioengineering of prevascularized dermo-epidermal skin grafts by using adipose tissue-derived endothelial cells (Stromal vascular fraction, SVF). The advantages of the SVF cells versus endothelial cells isolated from other tissue are the following: First, one single SVF biopsy delivers autologous stromal, vasculogenic, and mural cells in an ideal ratio. Second, SVF cells reveal a high vasculogenic potential across all age groups, even in elderly patients or with burns. Third, cells of the SVF can be isolated in a fully automated procedure, in large quantities so that they do not require in vitro expansion, and can be used freshly, e.g. for direct intraoperative use.

Grafts according to the present invention could be used to engineer any tissue in the human body, such as skin, cornea, cartilage, endothelia, valves etc.), or other structures such as glands, hair, nerves, muscles etc., and they could be used as testing tools for e.g. drug screenings.

The above mentioned prevascularized grafts according to a first aspect of the invention are suitable for research purposes, such as testing and screening, as well as for transplantation onto small animal models, such as e.g. mice and rats. According to the method of the present invention, fully functional lumen-forming human capillaries, both blood and lymphatic, can be engineered in hydrogels in vitro. However, e.g. for the testing on large animals, such as pigs and rabbits etc., or, more importantly, for clinical investigations in humans, larger, thinner and more mechanically stable constructs are required.

Therefore, according to a second, more advanced aspect of the invention, a method for the production of a tissue graft according to the above mentioned embodiments is provided, wherein additionally, after the seeding of the gel with cells of a first and/or a second type (or more types), the gel is compacted, preferably by compression.

Cell-seeded collagen gel has been shown (e.g. in EP 1 773 416 B1) to be an excellent biomimetic starting point for tissue equivalent implants, however, its mechanical weakness has been a drawback. By adding the step of gel compaction, one can make use of the optimal characteristics of a gel (e.g. made of collagen) without having to put up with its insufficiency in terms of mechanical strength. Thereby, very thin grafts, i.e. of tissue/organ physiological thickness can be produced without having to sacrifice mechanical strength. Not only does the compaction/compression increase the mechanical strength of a gel with a specific thickness, but the mechanical stability of very thin gels achieved by compaction/compression is even higher than the mechanical stability of gels with a much greater thickness.

According to an especially preferred embodiment of the invention, the gel is compacted by plastic compaction, preferably by compression in a compression device, preferably by applying a mechanical compressive force to the gel. Thereby, the density and mechanical strength of the scaffold matrix are increased.

Plastic compaction" in the sense of this application means deforming the gel to reduce its volume, such that the gel substantially retains its new volume, even after the cause of compaction is removed. The volume of the gel preferably is reduced by at least 40%, preferably up to 90%.

The compaction in terms of this description is a rapid, cell-independent process resulting from subjecting the gel to a physical treatment, such as an external force or pressure, which expels interstitial liquid from the gel. Plastic compaction therefore is independent of the action of cells which are cultured within the gel. The amount and the extent of the compaction may be varied according to the desired reduction in thickness of the gel.

The compaction of the gel can be carried out prior to or after the formation of the at least one first biostructure. For the preferred embodiment of a dermo-epidermal skin graft, the compaction is applied to the prevascularized gel. In other words, according to this preferred embodiment, the compression of the gel is carried out on a gel already containing vascular biostructures. Surprisingly, the development of the biostructures, i.e. in this case of the vascular plexus is not impacted by the plastic compaction/compression of hydrogel. Preferably, the gel is seeded with the cells of the third type (or more types) after the compaction of the gel. For example for the preferred embodiment of a dermo-epidermal skin graft, the epidermal structure on the gel surface would otherwise be damaged by the compression.

The gel in an uncompressed state has a first thickness, and the compaction is carried out until the gel reaches in a compressed state a second thickness of 3-20 times less, preferably about 10 times less than the first thickness. For the a dermo-epidermal skin graft, for example, the preferred thickness of the gel in a compressed state is about 0.7-1 mm, which corresponds to the physiological thickness of skin.

The gel can be co-cultured with the respective cells in a flask containing a suitable medium for the cell growth of the specific cell type(s). Preferably, the gel is removed from the flask for compression and returned to the flask after compression for further cultivation.

The present invention is further directed to a tissue graft comprising a gel, the gel comprising at least one first biostructure formed (in vitro) of cells of at least a first type and/or a second type in and/or on the gel, preferably in the gel. Preferably, the tissue graft further comprises at least one second biostructure formed of cells of at least a third type in/and or on the gel, preferably on the gel. Preferably, the cells of the first and/or the second and/or the third type (or more types) are of human origin, more preferably of autologous human origin.

Preferably, the graft was produced by a method according to one of the above mentioned embodiments.

The first and/or second biostructure is selected from the group of organ structure or tissue structure, preferably epithelial structure, including glandular-, placental- or amniotic epithelial structure; vascular-, preferably blood and/or lymphatic vessel structure; nervous structure; connective tissue structure, including bone structure, hair structure, nail structure, tooth structure, mesenchymal structure, muscular structure, adipose structure.

The first and/or the second biostructure preferably comprises cells selected from the group of: cells of endodermal origin, cells of mesodermal origin, cells of ectodermal origin, including the neural crest, cells of trophoblast origin, germ cells, stem cells, progenitor cells, genetically modified cells.

According to an especially preferred embodiment, the graft comprises autologous human endothelial cells and autologous human fibroblasts in the gel, preferably in a ratio of fibroblasts to endothelial cells of at least 3:7, more preferably of at least 2:3, most preferably about 1:1.

The first biostructure preferably is a vascular biostructure, preferably a vascular plexus of blood and/or lymphatic capillaries. The second biostructure preferably is an epidermal biostructure. Advantageously, the first biostructure is a vascular biostructure formed in the gel and the second biostructure is an epidermal biostructure formed on the gel.

In case the first biostructure is a vascular plexus of blood- and lymphatic capillaries in the gel, the lymphatic capillaries therein preferably have a continuous lumen of physiological size, preferably of 17-60 µm. These lumen-forming lymphatic capillaries preferably have anchoring filaments, preferably fibrillin anchoring filaments.

The gel forming the scaffold of the graft preferably is a fibrin or collagen hydrogel, preferably a collagen type I hydrogel. Preferably, the gel is a compacted, preferably compressed hydrogel. Preferably, the gel has been compressed in a device as disclosed in application EP 13174441.

Most preferably, the tissue graft is a dermo-epidermal skin graft, wherein preferably the cells comprised in the first biostructure are HDMECs or SVF cells and the cells comprised in the second biostructure are keratinocytes, preferably epidermal keratinocytes. Especially in case of a dermo-epidermal skin graft, the graft preferably has a thickness of 0.2-3 mm, preferably 0.7-1 mm.

Autologous bioengineered prevascularized dermo-epidermal skin grafts based on a hydrogel scaffold have shown the ability to regenerate in vivo. Indeed after transplantation, the preformed capillaries functionally connected to the recipient's vasculature and epidermal and dermal regeneration was greatly supported (Marino et al. 2014, Bioengineering dermo-epidermal skin grafts with blood and lymphatic capillaries, Sci Transl Med. 2014 Jan. 29; 6(221):221ra14; and Klar et al. 2014, Tissue-engineered dermo-epidermal skin grafts prevascularized with adipose-derived cells, Biomaterials. 2014 June; 35(19):5065-78).

The method according to the invention is particularly useful in the production of a tissue equivalent implant, or a device for implantation into an individual to repair or replace damaged or diseased endogenous tissue (tissue graft). Examples of such defective tissues include skin, nerve, tendons, cartilage, bone, urogenital elements, liver, cardiopulmonary tissues, kidney, ocular tissues, blood vessels, intestine, and glands. If the tissue graft is a dermo-epidermal skin graft, the damaged tissue preferably is skin tissue. When compared to non-vascularized skin grafts, dermo-epidermal skin grafts of vascularized hydrogels, have shown to faster and better regenerate in vivo, thus, they might be clinically applicable in the treatment of e.g. burn and other skin defects.

With the help of the present invention both human blood and lymphatic vessels can be engineered in one tissue or organ graft. The in vitro generated network of capillaries significantly supports perfusion of the dermal component, hence, providing rapid and efficient access to oxygen and nutrients, which assures rapid take, proliferation, and differentiation of the skin transplant (Böttcher-Haberzeth et al., Tissue engineering of skin, Burns 36, 450-460 (2010)). Bioengineering a preformed network of lymphatic capillaries into dermo-epidermal skin grafts should help circumvent seroma formation by improving lymphatic drainage and accelerating the establishment of tissue fluid homeostasis.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 6 shows a schematic representation of a production process of a compressed hydrogel containing vascular biostructures in two variations with respect to the sequence of steps, FIG. 7-10 photo documentation of the production of a compressed prevascularized tissue graft; wherein

DESCRIPTION OF PREFERRED EMBODIMENTS

Figure 1:
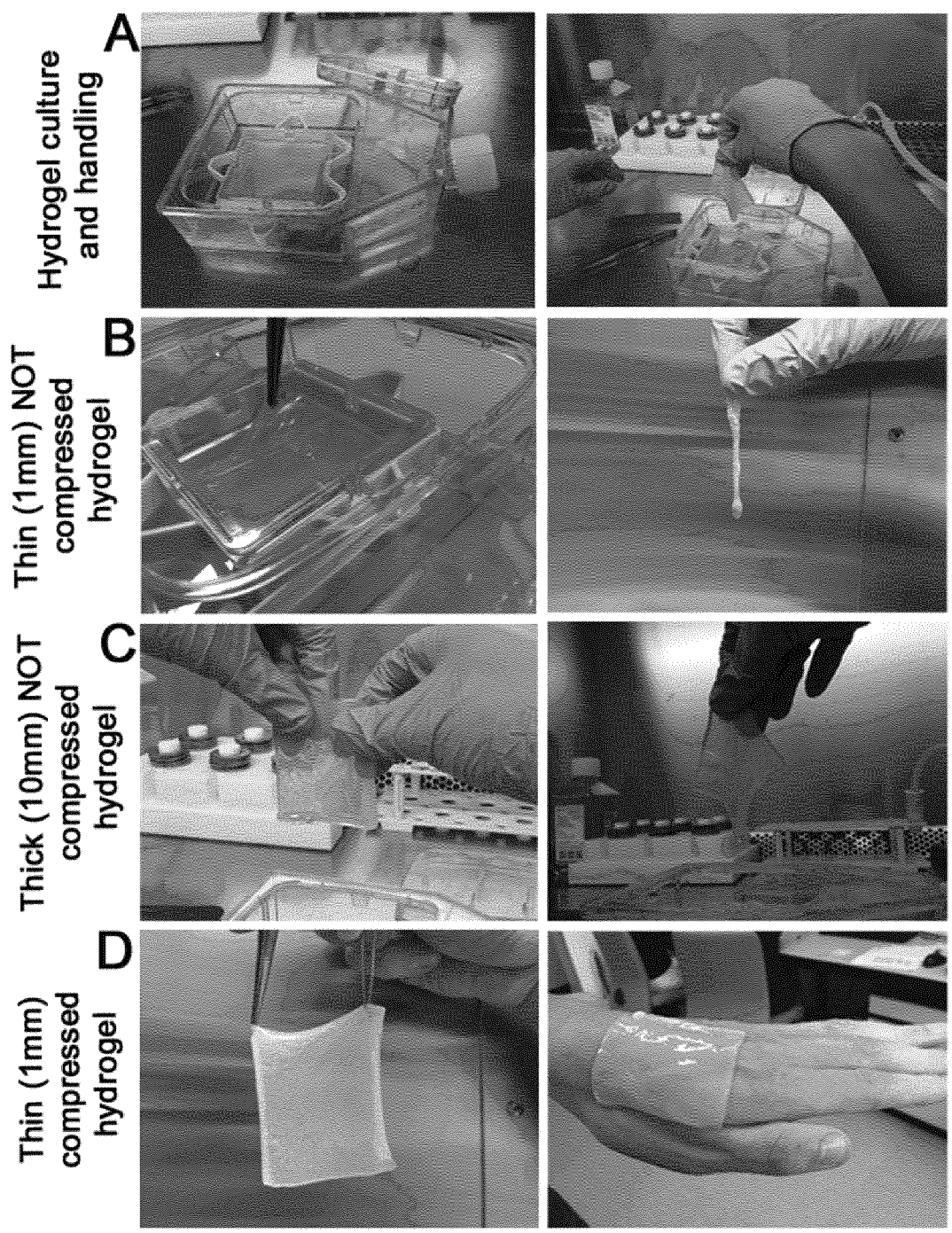
FIG. 1 shows the preparation of large hydrogels, wherein A.) shows hydrogel culture and handling in general; B.) shows the handling and consistency of a thin uncompressed hydrogel; C.) shows the handling and consistency of a thick uncompressed hydrogel; and D.) shows the handling and consistency of a thin compressed hydrogel.

The present invention is directed to a skin graft that, contrary to the prior art, doesn't just include patient's skin cells—it also contains both lymph and/or blood capillaries "prevascularized" ex vivo (in vitro) and then transplanted onto a wound. Dermo-epidermal skin grafts were created by taking HDMECs from human foreskin or SVF from human adipose tissue, and embedding them in three-dimensional hydrogels. Moving in vivo, the engineered skin grafts containing the HDMECs as well as human fibroblasts or SVF cells and keratinocyes were transplanted onto the wounded backs of nude rats (animals without a functional immune system). The human skin grafts formed the expected skin layers after 2 weeks and the capillaries functionally connected with existing rat capillaries. These engineered dermo-epidermal hydrogels potentially represent the next generation of skin grafts, complete with the blood and/or lymphatic vascular biostructures and ready to transplant.

EXAMPLE 1

Production of Uncompressed Prevascularized Dermo-Epidermal Skin Grafts Containing Blood and Lymphatic Capillaries The transplantation of human dermo-epidermal skin grafts containing vascular (blood and lymph) plexus onto rats was monitored. First, skin grafts were created in vitro using CD31 positive (CD31+) HDMECs, human CD90 positive (CD90+) fibroblasts, and human keratin5 positive (K5+) keratinocytes in fibrin hydrogels.

Both cell types constituting the dermal compartment of the graft were arranged underneath several layers of keratinocytes, the epidermal compartment (made visible and verified by confocal micrograph). These skin grafts were then transplanted onto wounded backs of immunoincompetent nu/nu rats using a Fusenig chamber to avoid competitive, lateral ingrowth/overgrowth of rat keratinocytes. Two weeks after transplantation, the human skin substitute was surgically removed from the rat underlying tissue and analysed for dermal structure and neovascularization. The vascularized neodermis supported stratification of the overlaying epidermis. Immunofluorescence analysis after 2 weeks revealed the presence of both human blood and lymphatic microvessels in the neodermis. Most of the bioengineered Prox1-positive/CD31-positive (Prox1+/CD31+) lymphatic microvessels maintained their lumen in vivo. Human microvessels expressing Lyve-1 and podoplanin were detected, indicating that human lymphatic capillaries remained intact 2 weeks after transplantation. Blood microvessels that solely expressed CD31 were also detected. Notably, the two distinct types of microvessels were never found to anastomose.

Further analysis of the capillary revealed that the human lymphatic microvessels presented fibrillin+ anchoring filaments, which strongly suggests that the capillaries could react to interstitial pressure variations and resolve tissue fluid accumulation in vivo. Furthermore, the bioengineered human lymphatic capillaries were devoid of mural cell coverage. Lymphatic drainage experiments were performed to investigate whether the bioengineered lymphatic capillaries would be functional in vivo. Small amounts (25 µl) of Evans blue were injected into grafts 15 days after transplantation. When analysing the grafts 30 min after injection, about five fold more Evans blue was retained in the hydrogels containing human fibroblasts only, compared with hydrogels containing human lymphatic and blood capillaries, indicating lymphatic drainage function in the prevascularized grafts. This data suggests that the grafted human lymphatics were recognized by and anastomosed to the recipient's lymphatics and that the newly developed lymphatic plexus efficiently drained fluid in vivo.

Materials and Methods for Example 1:

Human cells (keratinocytes, fibroblasts and endothelial cells) were isolated as described in Marino et al. 2014, Bioengineering Dermo-Epidermal Skin Grafts with Blood and Lymphatic Capillaries, Sci. Transl. Med. 6, 221ra14 (2014). In that study, first, hLECs were cocultured with human dermal fibroblasts within 3D hydrogels to investigate the capacity of LECs to develop into lumen-forming bona fide lymphatic capillaries. However, HDMECs-rather than LECs-were then used to engineer prevascularized dermo-epidermal skin substitutes. HDMECs were chosen because they are a mixture of dermal blood and LECs; hence, these cells have the potential to give rise to both types of capillaries.

Isolation and Culture of HDMECs and Dermal Fibroblasts:

HDMECs (human dermal microvascular endothelial cells) and human dermal fibroblasts were co-isolated from foreskins (n=8) obtained from the University Children's Hospital of Zurich after routine circumcisions. Foreskins were processed as described in Montario et al., Formation of human capillaries in vitro: The engineering of prevascularized matrices. Tissue Eng. Part A 16, 269-282 (2010). Isolated HDMECs and fibroblasts were co-cultured on 0.1% gelatin-coated dishes (Sigma-Aldrich) in endothelial cell growth medium-2 (EBM-2 MV with endothelial supplements; Lonza). Every day, fibroblasts were removed by mechanical scratching. FACS analysis for CD90 (Dianova) and CD31 (DakoCytomation) was used to calculate the number of fibroblasts and HDMECs (their ratio was 1:1 in all experiments). The cells were used at passage 1 in all experiments.

Generation of Capillaries in Hydrogels:

Fibrin or collagen hydrogels were produced with a Transwell system consisting of six-well culture inserts with membranes with 3-mm pores (BD Falcon). Briefly, for fibrin hydrogels, fibrinogen from bovine plasma (Sigma-Aldrich) was reconstituted in NaCl to a final concentration of 10 mg/ml, and then 11 ml of thrombin (Sigma-Aldrich, 100 U/ml) was added. For collagen hydrogels, membranes were covered with rat tail collagen type I hydrogels (3.2 to 3.4 mg/ml, BD Biosciences). The collagen matrix was prepared as described in Montario et al., 2010. To 1 ml of hydrogel solution, 100,000 human dermal cells (HDMECs/fibroblasts, 1:1) (initially, solely for investigation purposes, 60,000 hLEC's (as isolated according to Marino et al., 2014) in combination with 40,000 human dermal fibroblasts) were added and transferred into an insert for six-well plates. After clotting at room temperature, the preparations were incubated at 37° C. for 35 min in a humidified incubator containing 5% CO2 to ensure polymerization. At the end of the incubation period, culture medium was added to the upper and lower chambers [endothelial cell growth medium-2 (EBM-2 MV with endothelial supplements; Lonza)], and hydrogels were incubated for up to 3 weeks. Medium was changed every second day.

Testing for the Role of Fibroblasts in Lymphatic Vessel Formation:

As described in Marino et al., 2014, Fibrin hydrogels were produced as described above and cultured for 3 weeks in vitro. The hydrogels with 0 fibroblasts/100,000 LECs were cultured either in culture medium, in culture medium plus VEGF-A (40 ng/ml, Chemicon), in culture medium plus VEGF-C (100 ng/ml, R&D Systems), or in fibroblast-conditioned culture medium. The hydrogels with 10,000 fibroblasts/90,000 LECs or 40,000 fibroblasts/60,000 LECs were grown in culture medium. For the Transwell assay, 100,000 fibroblasts were seeded on the underside of the Transwell, whereas hydrogels with 100,000 LECs were cultured on top. The migration of a little number of fibroblasts was observed from the underside of the insert through the porous membrane intro the hydrogel. Culture medium was changed every day.

Capillary formation did not occur in the absence of fibroblasts. Likewise, neither fibroblast-conditioned medium, the addition of vascular endothelial growth factor-A (VEGF-A) or VEGF-C, nor the presence of fibroblasts on the underside of a Transwell system induced capillary formation in hLECs. Hence, the physical contact between human dermal fibroblasts and LECs was a requisite for the development of true branching lymphatic capillaries in the hydrogel. Histology revealed that the engineered capillaries developed a continuous lumen of physiological size (17 to 60 µm), measured on whole-mount specimens. The lymphatic nature of the capillaries was confirmed by double immunofluorescence staining performed on whole-mount hydrogel preparations. The bioengineered lymphatic capillaries expressed CD 31 and the lymphatic-specific nuclear transcription factor Prox1. Most of the capillaries showed a physiological size of the nuclei (10 µm in diameter). Two other lymphatic vascular markers, Lyve-1 and podoplanin, confirmed the lymphatic nature of the bioengineered human capillaries.

Figure 4:
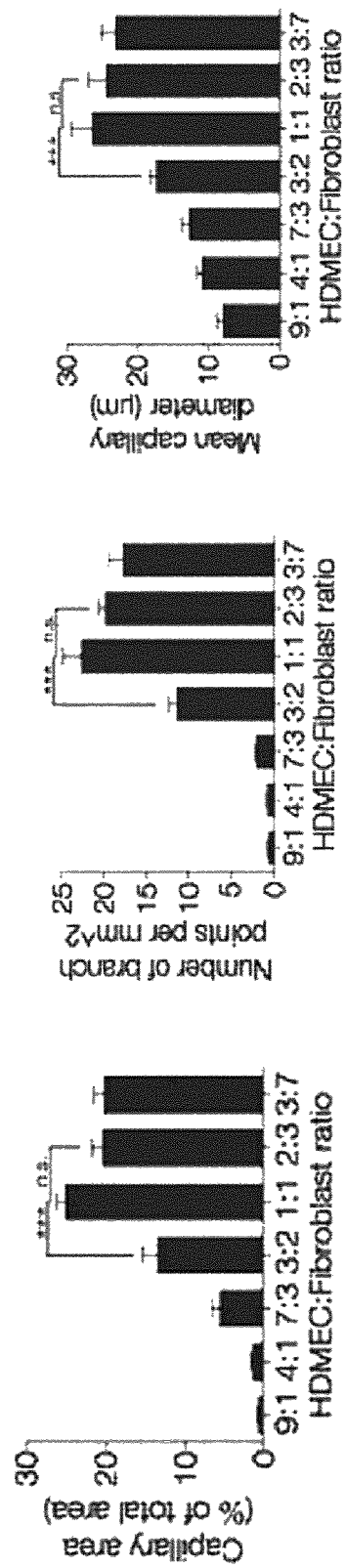
FIG. 4 shows, for uncompressed prevascularized tissue grafts, the ratio of endothelial cells (HDMECs) to dermal fibroblasts, in a.) with relation to the capillary area, in b.) with relation to the number of branch points per $mm^2$, and in c.) with relation to the mean capillary diameter in µm.

In the tests the results of which are shown in FIG. 4, the capillary area (FIG. 4a), the number of branch points per $mm^2$ (FIG. 4b) and the mean capillary diameter (FIG. 4c) was observed and quantified with respect to a varying ratio of endothelial cells (HDMECs) to fibroblasts. For all three parameters a.)-c.), the seeding of a ratio of endothelial cells to fibroblasts of 1:1 has shown to be the optimal ratio in terms of capillary formation in uncompressed gels, wherein ratios of 2:3 and 3:7 also showed positive results.

Preparation of Prevascularized Skin Grafts:

After 2 weeks of culture, 1 million human keratinocytes (isolated as described in Braziulis et al. 2012), were seeded on top of the prevascularized fibrin hydrogels. One week thereafter, transplantation or whole-mount immunostaining was performed.

Grafting Bioengineered Skin Grafts onto Immunoincompetent nu/nu Rats:

Immunoincompetent female nu/nu rats (Elevage Janvier) (n=12) were anesthetized by inhalation of 5% isoflurane (Baxter) and narcosis maintained by inhalation of 2.5% isoflurane via mask. Before the operation, buprenorphine (0.5 mg/kg) (Temgesic) for analgesia and retinol cream (Vitamin A "Blache"; Bausch & Lomb) for eye protection were applied. To prevent wound closure from the side and overgrowth of the human transplant by rat tissue, a special polypropylene ring (modified Fusenig chamber), 2.6 cm in diameter, was designed in our laboratory. The rings were sutured to full-thickness skin defects created on the back of the rats with nonabsorbable polyester sutures (Ethibond; Ethicon). Cultured prevascularized dermo-epidermal round skin grafts of about 2.6 cm in diameter, and a thickness of 3-8 mm were placed into the polypropylene rings and covered with a silicon foil (Silon-SES; Bio Med Sciences) and polyurethane sponges (Ligasano; Ligamed). Rats were sacrificed at 15 days after surgery. At sacrifice, dressings and sutures were removed, and multiple graft biopsies (n=12) were collected for different analyses.

EXAMPLE 2

Production of Uncompressed Prevascularized Dermo-Epidermal Skin Grafts Containing Blood Capillaries Generated by SVF Cells The transplantation of human dermo-epidermal skin grafts containing a blood vascular plexus onto rats was monitored. First, skin grafts were created in vitro using SVF cells and keratinocytes in fibrin hydrogels.

SVF cells were arranged underneath several layers of keratinocytes, the epidermal compartment (made visible and verified by confocal micrograph). These skin grafts were then transplanted onto wounded backs of immunoincompetent nu/nu rats using a Fusenig chamber to avoid competitive, lateral ingrowth/overgrowth of rat keratinocytes. Two weeks after transplantation, the human skin substitute was surgically removed from the rat underlying tissue and analysed for dermal structure and neovascularization. The vascularized neodermis supported stratification of the overlaying epidermis. Immunofluorescence analysis after 2 weeks revealed the presence of human blood in the neodermis. The bioengineered microvessels maintained their lumen in vivo and anastomosed, perfusing the graft, to the recipient's vasculature as early as 4 days after transplantation. This rapid perfusion triggered survival and functionality of the skin.

Materials and Methods for Example 2:

Human cells (keratinocytes and SVF cells) were isolated as described in Klar et al. 2014, Tissue-engineered dermo-epidermal skin grafts prevascularized with adipose-derived cells, Biomaterials. 2014 June; 35(19):5065-78. In that study, SVF cells were used to engineer prevascularized dermo-epidermal skin substitutes.

Cell Isolation and Culture:

Human subcutaneous adipose tissue samples were obtained either from lipoaspirates or fat excisions from healthy human donors (between 18 and 68 years of age), female or male, mostly from abdominal body location, all of them undergoing a surgical fat liposuction or excision operation. Lipoaspirates or excised fat samples were minced into small pieces and digested with 0.075% (W/V) type II collagenase (355 U/mg, Worthington, Lakewood, N.J., USA) for 60 min at 37° C. under shaking. After centrifugation at 200 g for 10 min, the oil and aqueous layers were discarded. The resulting pellet was washed in phosphate buffered solution (PBS, Gibco, Invitrogen, Carlsbad, Calif., USA) and passed through a 100 mm and 40 mm strainer. Red blood cells were lyzed by incubation for 2 min with a buffer containing 0.15 M/l ammonium chloride, 1.0 mM/l potassium bicarbonate (both Merck, Darmstadt, Germany), and 0.1 mM/l Na-EDTA (Fluka Analytical, Sigma-Aldrich Chemie GmbH, Buchs, Switzerland). After centrifugation and washing in PBS, the SVF cell pellet was resuspended in a complete medium (CM) consisting of a-Modified Eagle's Medium (a-MEM, Gibco) supplemented with 10% fetal bovine serum (FBS), 1% hepes, 1% sodium pyruvate and 1% penicillinestreptomycineglutamin (100×) solution (all from Gibco), stained with crystal violet (Sigma) and counted by using a Neubauer chamber. $1.6\text{-}0.9 \times 10^5$ nucleated cells were routinely isolated from 1 ml of a fat liposuction biopsy and $1\text{-}0.55 \times 10^5$ nucleated cells from 1 g of an excision biopsy. For monolayer expansion, SVF cells were seeded at a density of $2 \times 10^3$ cells/cm$^2$ onto tissue culture plates, cultured in CM supplemented additionally with 5 ng/ml FGF-2 (R&D Systems) and passaged at a density of $3 \times 10^3$ cells/cm$^2$ when confluent. The donor-matched, monolayer-expanded adipose-derived cells will be thereafter referred to as adipose stromal cells (ASC), to distinguish them from the population of freshly isolated SVF cells. Human dermal fibroblasts (HDF) and keratinocytes (KC) were isolated and expanded from foreskin (males between 2 and 18 years of age) as described in Pontiggia et al., Markers to evaluate the quality and self-renewing potential of engineered human skin substitutes in vitro and after transplantation. J. Invest. Dermatol. 2009; 129:480-90).

Preparation of Prevascularized Hydrogels:

Fibrin hydrogels were prepared using fibrinogen from bovine plasma (Sigma-Aldrich) reconstituted in 0.9% NaCl at a final concentration of 10 mg/ml. To achieve a comparable cell seeding inside the hydrogel, $3 \times 10^5$ SVF cells, $7.5 \times 10^4$ ASC, or $7.5 \times 10^4$ HDF per 3 ml gel. The concentration of SVF cells was optimized with respect to generating a functional and homogeneous dermal capillary plexus prior to transplantation. The corresponding prevascularized grafts started to be efficiently perfused 3-4 days after transplantation. The seeding density of the cells was normalized according to the number of mesenchymal cells, which were approximately four times higher in ASC than in the SVF. We seeded $1 \times 10^5$ SVF cells per lml of hydrogel to reconstitute the dermal skin Cells were centrifuged, resuspended in 100 ml EGM-2MV medium (Lonza, Basel, Switzerland) and mixed with 3 ml of the fibrinogen solution. The gels were placed in 6 well cell culture inserts with membranes of 3.0 mm pore-size (BD Falcon, Germany). Polymerization was initiated by adding 33 ml of thrombin (Sigma-Aldrich, 100 U/mL) and the gels were kept for 10 min at room temperature following by 1 h at 37° C. in a humidified incubator containing 5% $CO_2$. To prepare collagen hydrogels, rat collagen type I (BD Bioscience, Franklin Lakes, N.J., USA) was mixed with 0.2 ml neutralization buffer containing 0.15 M NaOH. After polymerization period, EGM-2MV was added to the upper and lower chambers of fibrin/collagen hydrogels, they were incubated for one or three weeks and analyzed for vascular network formation. To prepare dermo-epidermal skin substitutes (DESS) for transplantation, cells were cultured for two weeks in fibrin/collagen hydrogels in EGM-2MV medium, subsequently covered by keratinocytes ($7.5 \times 10^4$/gel), cultured for one additional week, and transplanted onto the immuno-incompetent rats. Stromal cells (with or without EC) formed the dermal compartment, whereas keratinocytes constituted the dominating cell type in the epidermal compartment of DESS. As the dermal compartment of vascDESS was prevascularized in vitro, it already contained a mature network of human engineered capillaries.

Transplantation of Tissue-Engineered Skin Substitutes:

The surgical protocol was approved by the local Committee for Experimental Animal Research (permission number 76/2011). Immuno-incompetent female nu/nu rats, eight to ten weeks old (Harlan Laboratories, The Netherlands), were prepared and anesthetized (as described in Pontiggia et al., 2009); three independent donors for SVF (n=6 per condition; 18 rats) and ASC (n=6 per condition; 18 rats), and four for HDF (n=4 per condition; 12 rats) (in total 48 rats) (Schneider et al., Matriderm versus Integra: a comparative experimental study. Burns 2009; 35:51-7). DESS were transplanted onto full-thickness skin defects created surgically on the backs of the rats. To protect the transplants and to prevent wound closure from surrounding rat skin, custom made steel rings (diameter 2.6 cm) were sutured into full-thickness skin defects created on the backs of the rats, using non-absorbable polyester sutures (Ethibond, Ethicon, USA). The transplants were then covered with a silicone foil (Silon-SES, BMS, USA), a polyurethane sponge (Ligasano, Ligamed, Austria), a cohesive conforming bandage (Sincohaft, Theo Frey AG, Switzerland), and tape as wound dressing. By these means the bandaged site was fully protected and the rat could not scratch the transplant. Dressing changes and photographic documentations were performed once per week. After 4, 7, and 14 days the transplanted skin analogs were excised in toto and processed for cryo- and paraffin sections, and electron microscopy.

EXAMPLE 3

Production of Compressed Prevascularized Dermo-Epidermal Skin Grafts

Materials and Methods for Example 3:

Human cells (keratinocytes, fibroblasts and endothelial cells) were isolated as described above. Tissue grafts were prepared from hydrogels of 7×8 cm size as described below with reference to FIGS. 7-10. To obtain mechanical stability, modified plastic compression was performed with the compression device according to EP 13 174 441.

Figure 7:
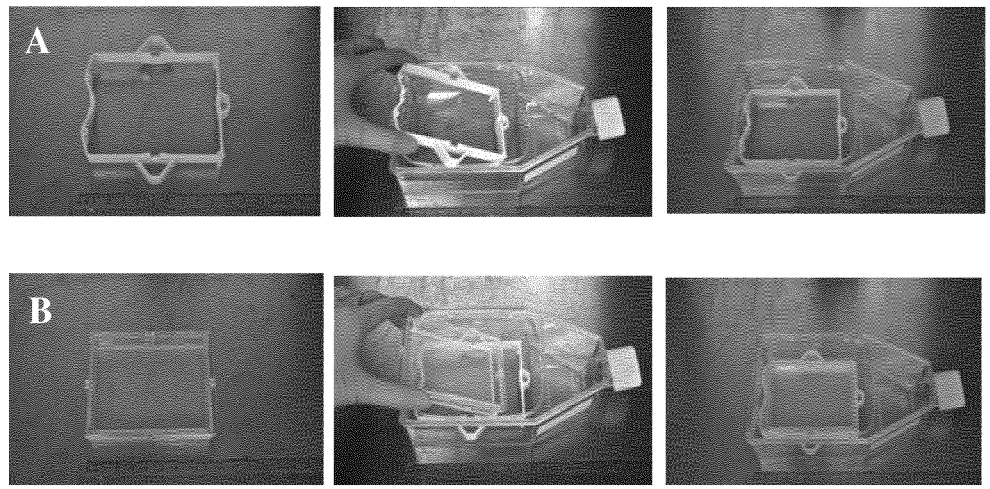
FIG. 7 shows a photo documentation of flask assembly and hydrogel preparation.

Preparation of the Hydrogel (as shown in FIG. 7):

As shown in FIG. 7, an insert frame (A) and an insert (B) are placed into a tissue culture flask of 115 cm2. 1 million fibroblasts/endothelial cells (ratio 1:1) are resuspended in 4 ml endothelial cell medium ("cells"). 18±1 ml of collagen hydrogel is poured in a tube ("hydrogel"). 850 µl of Acetic acid filtered are added to the "hydrogel" ("mixture"). The "mixture" is mixed by gently pivoting the tube.

Addition of 7.5±0.2 ml of Reconstitution buffer to the cells ("cells+RB") (the reconstitution buffer comprising Aqua ad injectabilia, Sodium hydroxide, Sodium hydrogen carbonate, HEPES Buffer; Reference for original recipe: Costea et al: Crucial Effects of Fibroblasts and Keratinocyte Growth Factor on Morphogenesis of Reconstituted Human Oral Epithelium. J Invest Dermatol 121:1479-1486, 2003)

"cells+RB" is mixed by gently inverting the tube.

"cells+RB" is transferred into the "mixture": ("final hydrogel")

"final hydrogel" is mixed by gently inverting the tube

"final hydrogel" is poured into the insert in the flask (B)

Gelling:

The flask is incubated for 10±2 min at room temperature (18-26° C.), followed by incubation for 30±1 min at 37±1° C.

Figure 8:
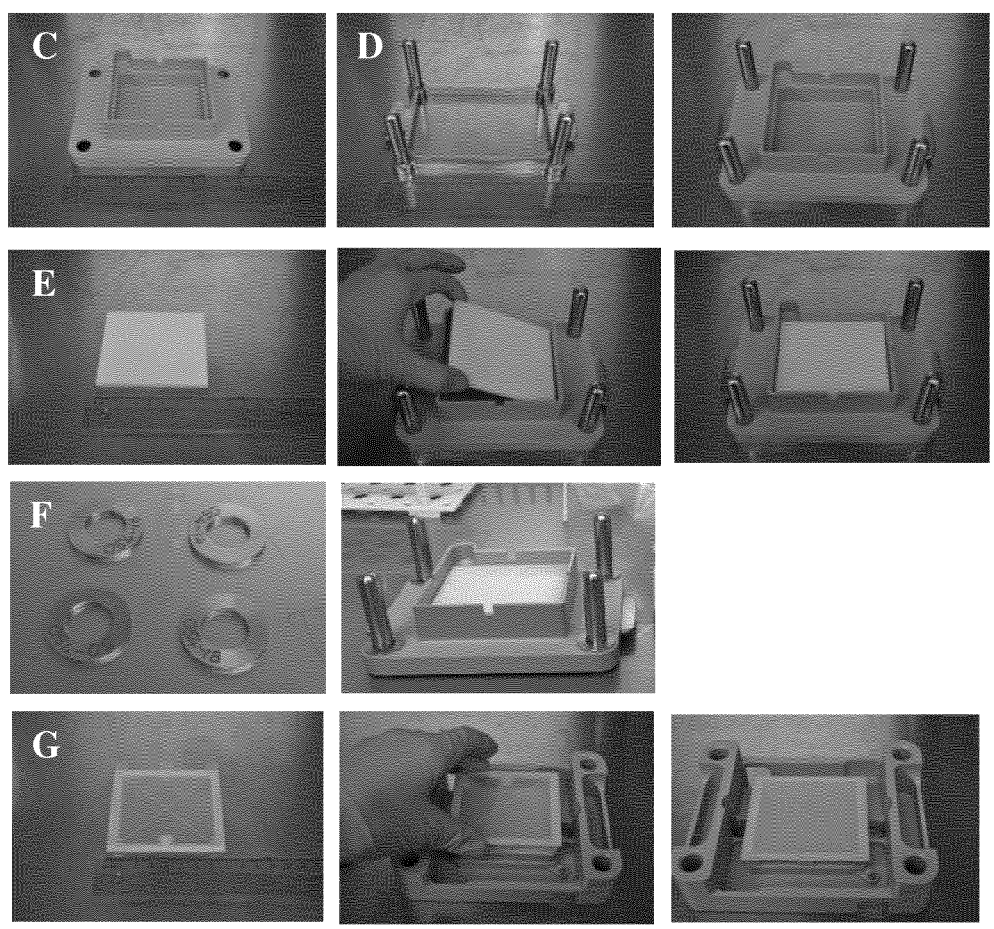
FIG. 8 shows a photo documentation of assembly of the compression device.

Assembly of Compression Device (as shown in FIG. 8):

To obtain mechanical stability, modified plastic compression was performed with the compression device according to EP 13 174 441, as shown in FIG. 8:

The base tray (C) is placed onto the base frame (D)

The porous plate (E) plate is placed into the base tray

The spacers (F) are placed onto the base tray

The piston plate (G) is placed onto the top plate

Figure 9:
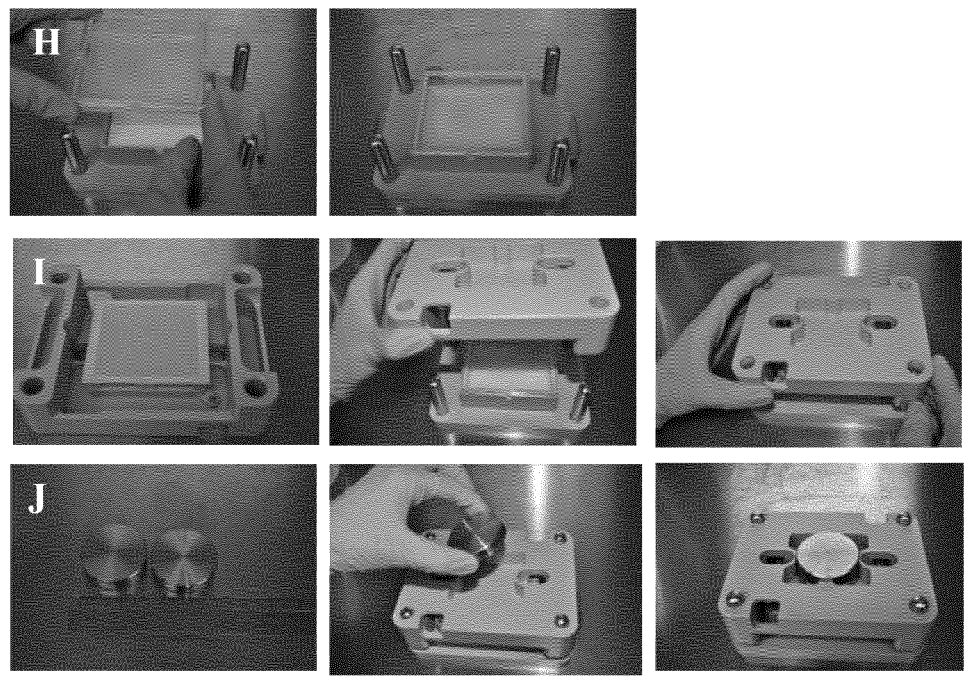
FIG. 9 shows a photo documentation of the compression step
Figure 10:
FIG. 10 shows a photo documentation of the gel transfer step.

Compression (as shown in FIG. 9):
The insert of the flask is transferred into the compression device (H)
The top plate with the piston plate (I) is added to the compression device
The 3 compression weights (J) are successively added to the compression device: 150 g for 5 min, then 150 g+200 g for 5 min, then 150 g+200 g+500 g for 5 min Gel Transfer (as shown in FIG. 10):
After 15±1 min compression time, the compression success is visually checked
The compression weights are removed from the compression device
The piston plate is unlocked from the top plate (click mechanism)
The top plate is removed from the compression device with the piston plate remaining in the insert
The piston plate is removed from the membrane insert lifting it carefully first on one side an then on the other side without disturbing the hydrogel (K)

Gel Cultivation:
The insert with the gel is transferred into the insert frame of the flask
90 ml of endothelial cell medium are added to the flask base (within the barrier). The hydrogel must be fully submerged in the medium
10 ml of endothelial cell medium are added onto the gel (within the insert). The hydrogel must be fully submerged in the medium
The flask is stored in the incubator for 21 days to allow the vascular biostructure formation Keratinocyte Seeding:
8 million Keratinocytes are prepared and resuspended in 10±2 ml keratinocyte medium
the medium on top of the gel is aspirated
the medium below the gel is aspirated
90±5 ml of endothelial cell medium are added to the flask base (within the barrier). The gel must be fully submerged in the medium
10±2 ml of keratinocyte medium are added onto the gel (within the insert). The gel must be fully submerged in the medium
The flask is stored in the incubator for 2-4 days to allow keratinocyte attachment and proliferation
The last proliferation step is then followed by either in vivo transplantation

OR

Air Liquid Phase for Epidermal Biostructure Formation:
Keratinocytes are cultured for 4 days in keratinocyte medium. Then, the keratinocyte layer is raised to the air/liquid interface and cultured for 3 additional weeks (according to Air liquid stratification protocol: Pontiggia L et al. Journal of Investigative Dermatology (2009) 129, 480-490; doi:10.1038/jid.2008.254; published online 21 Aug. 2008)

Analysis:
The morphology and functionality of the lymphatic microvessels were characterized and analysed both in vitro and in vivo with immunofluorescence and histology. Histological and whole mount analysis was performed as described in Marino et al. 2014.

FIG. 1 shows the differences in handling between different types of hydrogels. A.) Large hydrogels (7×8 cm, collagen type 1) were prepared in combination with cells and cultured in flasks which allowed their removal for further processing. B.) So far, if a thin hydrogel needed to be created, for example to reach the thickness of human skin (0.7-1 mm), its poor mechanical stability was a dramatic problem. C.) Thicker hydrogels of about 10 mm thickness presented higher mechanical stability, but they were not suited for most of the tissue engineering purposes. D.) Plastic compaction/compression allows the bioengineering of thin, large, mechanically stable hydrogel based tissue products.

Figure 2:
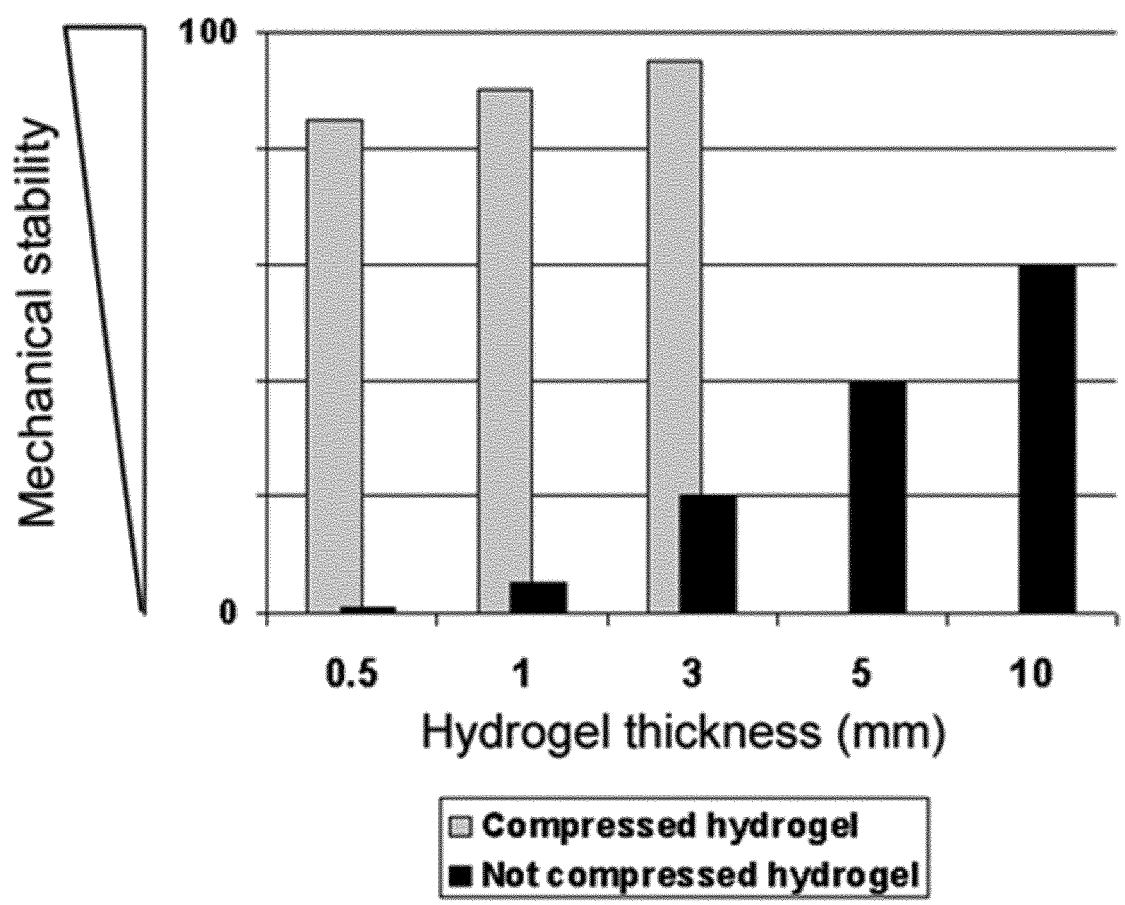
FIG. 2 shows the correlation of mechanical stability and hydrogel thickness in a schematic bar chart.

FIG. 2 shows the relation between mechanical stability and hydrogel thickness for compressed hydrogels versus uncompressed hydrogels. In uncompressed hydrogels (black columns), the mechanical stability increases with increasing hydrogel thickness. In compressed hydrogels of the same thickness of about 0.5 mm, the mechanical stability is about 80 fold higher. The human skin has a thickness of about 0.7-1 mm, which is why this range of hydrogel is especially interesting. According to the diagram of FIG. 2, compressed hydrogels of 0.5-3 mm thickness presented a much higher mechanical stability than uncompressed hydrogels of the same thickness, and even higher than the mechanical stability of uncompressed hydrogels of 10 mm thickness.

Figure 3:
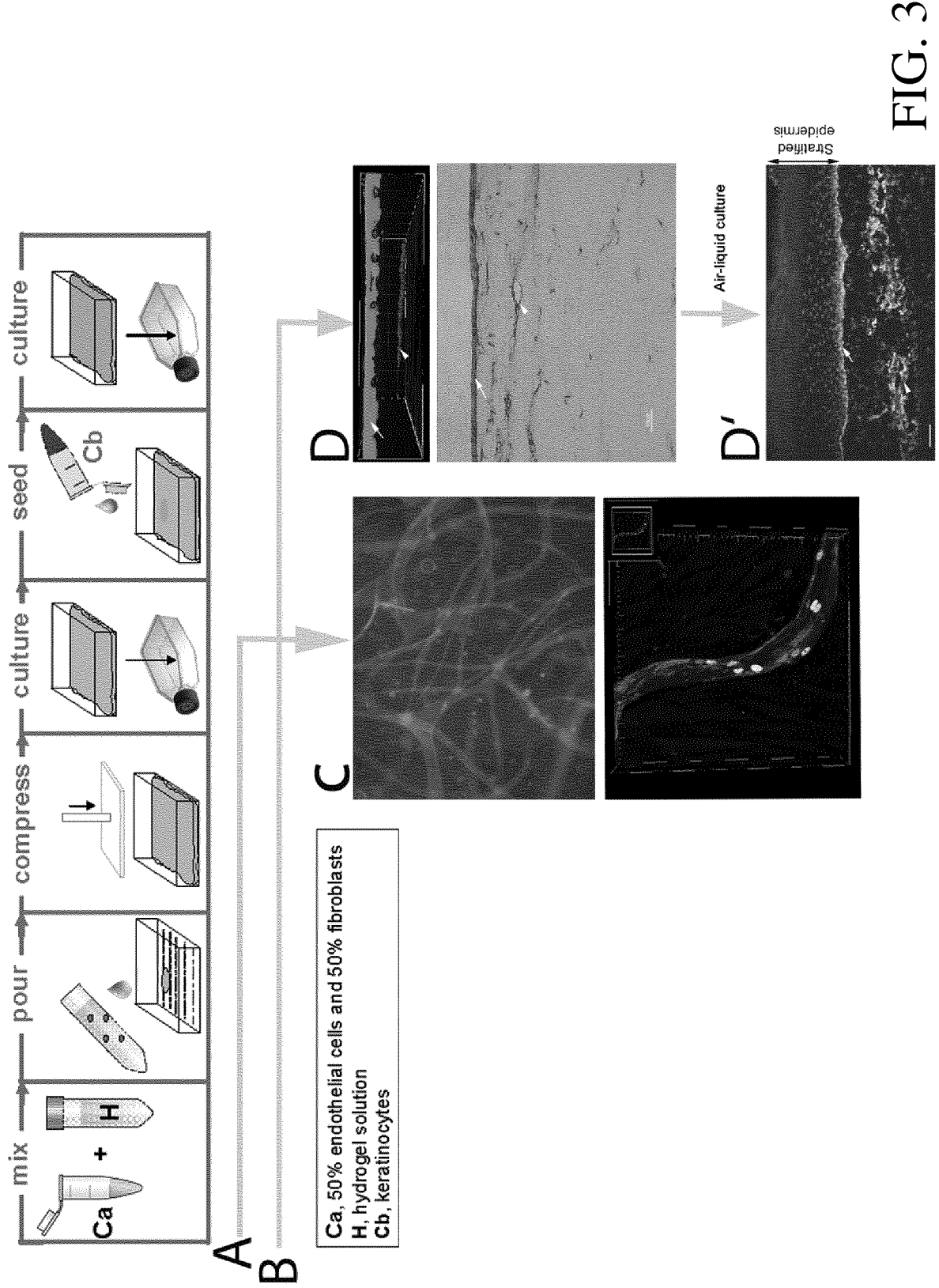
FIG. 3 shows a schematic representation of the production process of hydrogels containing vascular structures; first by showing the sequence of steps for production of large compressed hydrogels containing vascular structures (A); and of large vascularized dermo-epidermal skin grafts (B); followed by the results of such methods in immunofluorescence studies (C, D-upper panel, D') and histological sectioning (D-lower panel).

FIG. 3 shows that compressed hydrogels can be created in combination with vascular and epidermal bio-structures. At the top, the production process of hydrogels containing vascular structures and vascularized dermo-epidermal skin grafts is depicted. The first arrow marked with A shows that four steps are necessary for the creation of large compressed hydrogels containing vascular structures (mix, pour, compress, culture). The second arrow marked with B shows that for the engineering of large vascularized dermo-epidermal skin grafts based on compressed hydrogels, all six depicted steps are necessary (mix, pour, compress, culture, seed, culture). In the two pictures labelled with C, the vascular structures are visualized by whole mount immunofluorescence for an endothelial marker (CD31) and a nuclear lymphatic marker (Prox 1) 21 days after seeding. In the upper, first picture, many vascular structures are made visible. This confirms that HDMECs organize into vascular structures. In the lower, second picture, only lymphatic vessels are made visible. This confirms that HDMECs isolated from human foreskin contain both Prox1 positive lymphatic and Prox1 negative blood vascular endothelial cells. In the pictures labelled with D, the first, upper picture shows a whole mount immunofluorescence for CD31 and a keratinocyte marker (Citokeratin 5), making visible the vascular structures (arrow heads) in the skin grafts below a layer of keratinocytes (arrow). The second, lower picture shows a histological sectioning making visible the epidermal layer and the capillaries with lumen. If the hydrogels are further cultured under air-liquid conditions, the formation of an epidermal biostructures occurs: In the picture labelled with D', immunofluorescence analysis shows a stratified epidermis with a basement membrane deposition (arrow) is depicted. This epidermis is growing on the hydrogel containing the vascular biostructures (arrow head)

Figure 5:
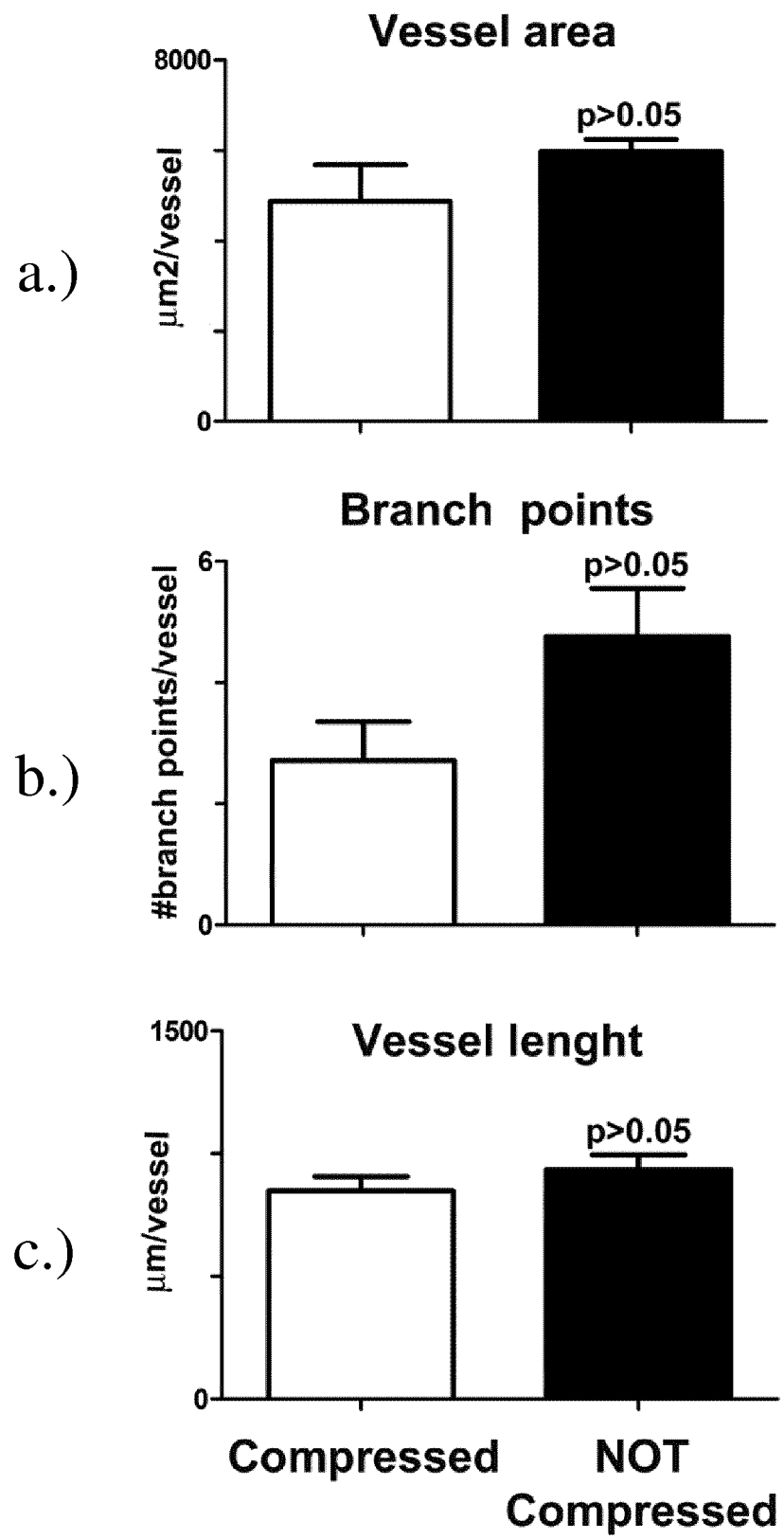
FIG. 5 shows unvaried vessel characteristics in compressed versus uncompressed hydrogels; wherein a.) shows the vessel area; b.) shows the amount of branch points; and c.) shows the vessel length.

FIG. 5 shows that vessel characteristics remain unvaried in compressed (white bars) versus NOT compressed hydrogels (black bars). Vessel formation occurred in both compressed and NOT compressed hydrogels. Quantitative analysis showed that the vessel area and the number of branch points were greater in the NOT compressed hydrogels as compared to compressed. However, statistical analysis showed a non-significant difference (p>0.05). Vessel length remained unvaried. Surprisingly, this showed that the development of the vascular plexus was not impacted by the plastic compaction/compression of the hydrogels.

Figure 6:
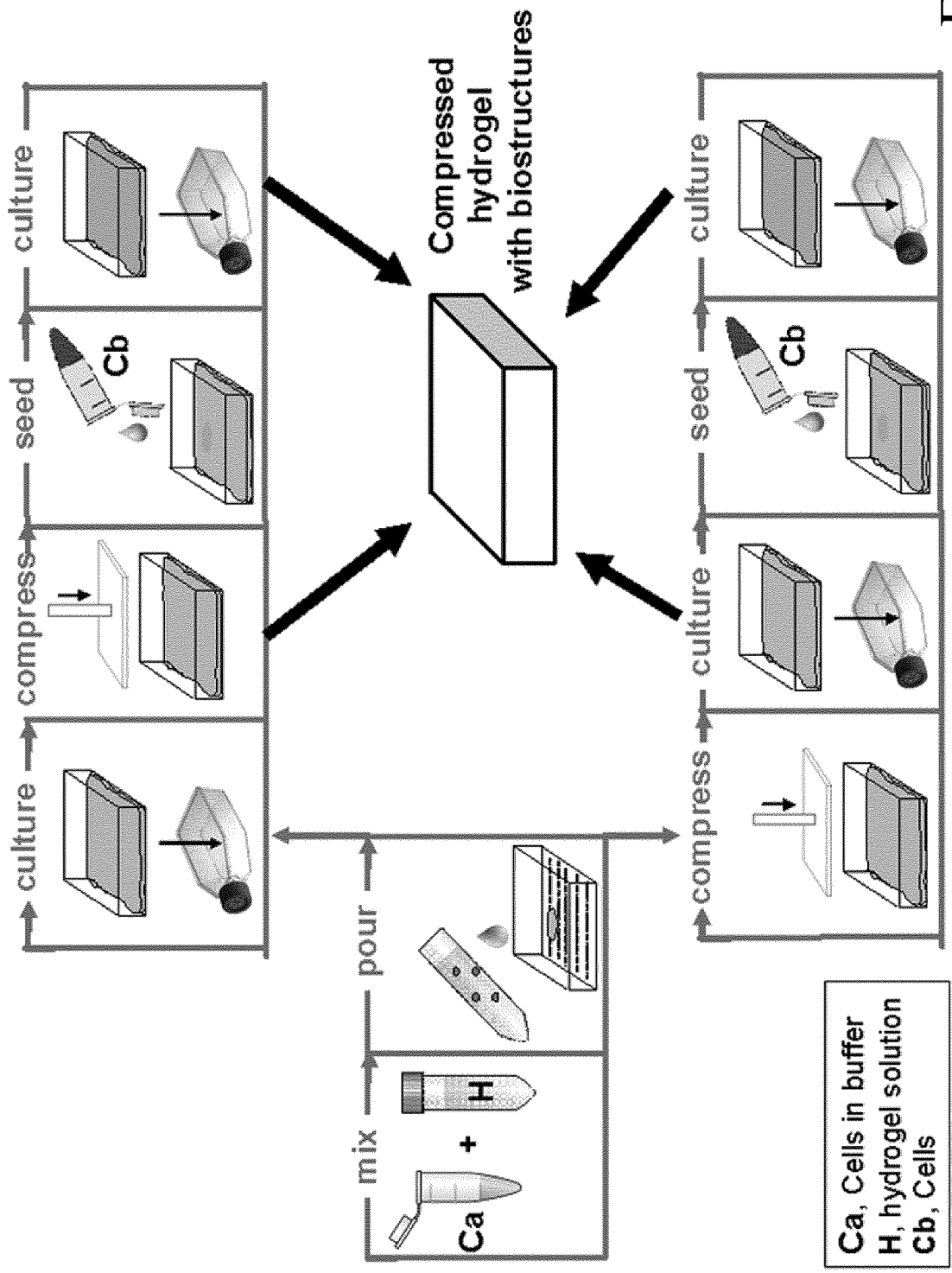

In FIG. 6, the top row shows the production sequence of FIG. 3. However, it is possible to invert the steps of compression and culture of the Ca-cells (cells of the first and/or second type seeded for the formation of the first biostructure). Other tissues can be engineered using other cells to produce other biostructures in compressed hydrogels. Compression can be perfomed prior or post structure formation. Tissue grafts produced by including the compression step are useful for all kind of thin tissues, such as skin, cornea, cartilage, membranes, endothelium, mucosa etc.

The method of the present invention shows that, besides blood capillaries (which can be generated by HDMECs or SVF cells), functional lymphatic capillaries can be generated using three dimensional hydrogels. Like normal lymphatics, these capillaries branch, form lumen, and take up fluid in vitro and in vivo after transplantation onto immunocompromised rodents. Formation of lymphatic capillaries could be modulated by both lymphangiogenic and anti-lymphangiogenic stimuli, demonstrating the potential usefulness of this system for in vitro testing. Blood and lymphatic endothelial cells never intermixed during vessel development, nor did blood and lymphatic capillaries anastomose under the described circumstances. After transplantation of the engineered grafts, the human lymphatic capillaries anastomosed to the nude rat's lymphatic plexus and supported fluid drainage. This data suggests that these skin grafts/substitutes with physiological, structural, and functional properties could one day be applied on patients suffering from severe skin defects.

The invention claimed is:

1. A dermo-epidermal skin graft comprising a gel, the gel comprising at least one first biostructure formed of cells of at least a first type, and cells of a second type in or on the gel, and a second biostructure comprising cells of at least a third type in or on the gel,
   wherein the gel is a compacted hydrogel, and
   wherein the cells comprised in the first biostructure are SVF cells or a mixture of endothelial cells and fibroblasts, and
   wherein the cells comprised in the second biostructure are keratinocytes,
   wherein the first biostructure is a vascular biostructure, and
   wherein the second biostructure is an epidermal biostructure.

2. The dermo-epidermal skin graft according to claim 1, wherein the cells of the first or the second or the third type are of human origin.

3. The dermo-epidermal skin graft according to claim 1, wherein the tissue graft comprises autologous human endothelial cells and autologous human fibroblasts in the gel.

4. The dermo-epidermal skin graft according to claim 1, wherein the first biostructure is a vascular biostructure in the gel and the second biostructure is an epidermal biostructure on the gel.

5. The dermo-epidermal skin graft according to claim 1, comprising lumen-forming lymphatic capillaries.

6. The dermo-epidermal skin graft according to claim 1, wherein the gel is a fibrin or collagen hydrogel.

7. The dermo-epidermal skin graft according to claim 1, wherein the graft has a thickness of 0.2-3 mm.

8. The dermo-epidermal skin graft according to claim 1, wherein the compacted hydrogel is compressed.

9. The dermo-epidermal skin graft according to claim 1, wherein the second biostructure is formed of cells of at least a second and/or a third type on the gel.

10. The dermo-epidermal skin graft according to claim 2, wherein the cells of the first or the second or the third type are of autologous human origin.

11. The dermo-epidermal skin graft according to claim 1, wherein the first or second biostructure are a blood or lymphatic vessel structure.

12. The dermo-epidermal skin graft according to claim 3, wherein the autologous human endothelial cells and autologous human fibroblasts in the gel are present at a ratio of fibroblasts to endothelial cells of at least 3:7.

13. The dermo-epidermal skin graft according to claim 1, wherein the vascular biostructure is a vascular plexus of blood and lymphatic capillaries.

14. The dermo-epidermal skin graft according to claim 1, wherein the graft has a physiological size is 17-60 µm.

15. The dermo-epidermal skin graft according to claim 5, wherein the lymphatic capillaries have anchoring filament.

16. The dermo-epidermal skin graft according to claim 15, wherein the anchoring filaments are fibrillin anchoring filaments.

17. The dermo-epidermal skin graft according to claim 6, wherein the collagen hydrogel is a collagen type I hydrogel.

18. The dermo-epidermal skin graft according to claim 1, wherein the keratinocytes are human epidermal keratinocytes.

19. The dermo-epidermal skin graft according to claim 7, wherein the graft has a thickness of 0.7-1 mm.52.

20. The dermo-epidermal skin graft according to claim 5, wherein the lymphatic capillaries have a continuous lumen of physiological size.

* * * * *